United States Patent
Tan

(10) Patent No.: US 10,155,911 B2
(45) Date of Patent: Dec. 18, 2018

(54) METHOD OF REDUCING HYDROGEN SULFIDE LEVELS IN GASEOUS MIXTURES USING TRIAZINES

(71) Applicant: Dow Global Technologies LLC, Midland, MI (US)

(72) Inventor: Runyu Tan, Richwood, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/554,896

(22) PCT Filed: Apr. 4, 2016

(86) PCT No.: PCT/US2016/025820
§ 371 (c)(1),
(2) Date: Aug. 31, 2017

(87) PCT Pub. No.: WO2016/167994
PCT Pub. Date: Oct. 20, 2016

(65) Prior Publication Data
US 2018/0044598 A1 Feb. 15, 2018

Related U.S. Application Data

(60) Provisional application No. 62/148,452, filed on Apr. 16, 2015.

(51) Int. Cl.

| | | |
|---|---|---|
| *C10G 29/28* | (2006.01) | |
| *B01D 53/14* | (2006.01) | |
| *B01D 53/52* | (2006.01) | |
| *C07D 251/04* | (2006.01) | |
| *C10G 29/20* | (2006.01) | |
| *C10L 3/10* | (2006.01) | |

(52) U.S. Cl.
CPC ......... *C10G 29/28* (2013.01); *B01D 53/1468* (2013.01); *B01D 53/1493* (2013.01); *B01D 53/52* (2013.01); *C07D 251/04* (2013.01); *C10G 29/20* (2013.01); *C10L 3/103* (2013.01); *B01D 2252/202* (2013.01); *B01D 2252/2023* (2013.01); *B01D 2252/20415* (2013.01); *B01D 2252/20436* (2013.01); *B01D 2252/60* (2013.01); *B01D 2252/602* (2013.01); *B01D 2256/24* (2013.01); *B01D 2257/304* (2013.01); *B01D 2257/306* (2013.01); *C10G 2300/207* (2013.01); *C10L 2290/545* (2013.01)

(58) Field of Classification Search
CPC ............ B01D 53/1468; B01D 53/1493; B01D 2252/2023; B01D 2252/20415; B01D 2252/20436; B01D 2252/60; B01D 2252/202; B01D 2252/602; B01D 2256/24; B01D 2257/304; B01D 2257/306; B01D 53/52; C10G 29/20; C10G 2300/207; C10G 29/28; C10L 3/103; C10L 2290/545; C07D 251/04; C07C 4/02; C07C 9/04; C07C 11/24; C07C 2/76; C07C 2/78; C07C 5/09; C07C 11/04; C07C 2529/068; C07C 7/005; C07C 7/148
See application file for complete search history.

(56) References Cited

U.S. PATENT DOCUMENTS

| | | | |
|---|---|---|---|
| 4,748,011 A | 5/1988 | Baize | |
| 4,978,512 A | 12/1990 | Dillon | |
| 5,128,049 A | 7/1992 | Gatlin | |
| 5,347,004 A | 9/1994 | Rivers et al. | |
| 5,774,024 A | 6/1998 | Marusawa et al. | |
| 6,063,346 A | 5/2000 | Luna | |
| 6,942,037 B1 * | 8/2005 | Arnold et al. | .......... E21B 37/06 166/312 |
| 8,512,449 B1 | 8/2013 | Zaid et al. | |
| 8,734,637 B2 | 5/2014 | Taylor | |

FOREIGN PATENT DOCUMENTS

WO     9201481     2/1992

* cited by examiner

*Primary Examiner* — Sharon Pregler

(57) ABSTRACT

The present invention relates to a scavenging composition capable of scavenging a wide variety of sulfur-bearing compounds, such as hydrogen sulfide and method of use thereof. Said scavenging composition comprises an aqueous solution of a triazine compound, an anionic surfactant, and optionally an alcohol and/or glycol ether solution. The composition may be used in any kind of sulfide-scavenging operation and is particularly useful for sulfide scavenging in the context of sulfide removal from oil or gas streams and in the treatment of oil or gas transmission lines or equipment.

7 Claims, No Drawings

METHOD OF REDUCING HYDROGEN SULFIDE LEVELS IN GASEOUS MIXTURES USING TRIAZINES

FIELD OF THE INVENTION

The present invention relates to aqueous sulfide-scavenging compositions and method of use thereof useful for reducing or essentially eliminating $H_2S$ and other objectionable sulfides from hydrocarbon streams or transmission lines and equipment for such products. More particularly, the scavenging composition of the present invention is an aqueous solution comprising a triazine compound, an anionic surfactant, and optionally an alcohol and/or glycol ether.

BACKGROUND OF THE INVENTION

This invention relates generally to the treatment of gaseous mixtures such as sour gas to remove or reduce the levels of hydrogen sulfide therein. In the drilling, production, transport, storage, and processing of crude oil, including waste water associated with crude oil production, and in the storage of residual fuel oil, hydrogen sulfide and mercaptans are often encountered. The presence of hydrogen sulfide and mercaptans is objectionable because they often react with other hydrocarbons or fuel system components. Further, hydrogen sulfide and mercaptans are often highly corrosive as well as emit highly noxious odors. The toxicity of hydrogen sulfide in hydrocarbon streams is well known in the industry and uncontrolled emissions of hydrogen sulfide gives rise to severe health hazards. Burning of such vapors neither solves toxic gas problems nor is economical since light hydrocarbons have significant value. Considerable expense and efforts are expended annually to reduce the content of hydrogen sulfide in hydrocarbon streams to a safe level.

Nonregenerative scavengers for small plant hydrogen sulfide removal fall into four general categories: 1) aldehyde based, 2) metallic oxide based, 3) caustic based, and 4) other processes. In the removal of hydrogen sulfide by nonregenerative compounds, the scavenger reacts with the hydrogen sulfide to form a nontoxic compound or a compound, which can be removed from the hydrocarbon. For example, when formaldehyde reacts with hydrogen sulfide, a chemical compound known as form thionals (e.g., trithiane) is formed.

In large production facilities, it is generally more economical to install a regenerative system for treating sour gas streams. These systems typically employ a compound used in an absorption tower to contact the produced fluids and selectively absorb the hydrogen sulfide and possibly other toxic materials such as carbon dioxide and mercaptans. The absorption compound is then regenerated and reused in the system. Typical hydrogen sulfide absorption materials include alkanolamines, PEG, hindered amines, and other species that can be regenerated.

Treatments for removal of sulfhydryl compounds, such as hydrogen sulfide and mercaptans, from hydrocarbons and other substrates include the use of various reactive organic compounds. For example, U.S. Pat. No. 6,063,346 discloses the use of a combination of maleimides, formaldehydes, amines, carboxamides, alkylcarboxyl-azo compounds, and cumine-peroxide compounds for the removal of hydrogen sulfide and mercaptan contaminants from a fluid. Further, U.S. Pat. No. 5,128,049 discloses the use of certain morpholino and amino derivatives for the removal of hydrogen sulfide content from fluids. Low molecular weight aldehydes may also be combined with an alkyl or alkanolamine as disclosed in U.S. Pat. No. 4,748,011. Other aldehyde derived scavengers include the reaction product of low molecular weight alkanolamines and aldehydes as disclosed in U.S. Pat. No. 4,978,512.

PCT Application WO 92/01481 discloses a method of reducing sulfides in a sewage gas using certain tri-substituted-hexahydro-s-triazines. U.S. Pat. No. 5,347,004 discloses the use of 1,3,5 alkoxyalkylene hexahydro triazines. U.S. Pat. Nos. 5,128,049; 6,063,346; 8,512,449; and 8,734,637 disclose the use of triazines to remove hydrogen sulfide. U.S. Pat. No. 5,774,024 discloses the combination of an alkyl triazine scavenger and quaternary ammonium salt, where the quaternary ammonium salt enhances the effectiveness of the alkyl-triazine.

There is a continuing need for alternatives which may be useful in the removal and/or reduction of hydrogen sulfide from gaseous mixtures. Such alternatives include the development of new scavengers which are quick acting and which exhibit high affinity for removing hydrogen sulfide.

SUMMARY OF THE INVENTION

The present invention is a method of reducing $H_2S$ in a liquid or gaseous stream comprising $H_2S$ which comprises contacting the stream with an aqueous sulfide-scavenging composition comprising: (a) one or more triazine compound of the formula:

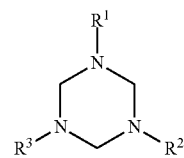

wherein $R^1$, $R^2$, and $R^3$ are independently selected from a $C_1$ to $C_{20}$ straight or branched chain alkyl group,

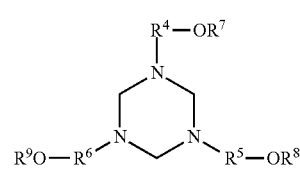

wherein $R^4$, $R^5$, and $R^6$ are independently selected from a $C_1$ to $C_6$ alkyl group and wherein $R^7$, $R^8$, and $R^9$ are independently selected from hydrogen or a $C_1$ to $C_6$ alkyl group, and (b) an anionic surfactant, wherein the amount of the anionic surfactant is sufficient to accelerate the $H_2S$ scavenging action of the triazine compound in comparison with the scavenging action of said triazine without the surfactant compound.

In one embodiment of the method disclosed herein above the preferred triazine compound (a) is 1,3,5-trimethyl-hexahydro-1,3,5-triazine, more preferably 1,3,5-tris(2-hydroxyethyl)hexahydro-s-triazine.

In one embodiment of the method disclosed herein above the anionic surfactant (b) is selected from a dialkyl sulfosuccinate, a di-sulfonate, an alkylbenzene sulfonate, an alkyl sulfate, a carboxylic acid, or mixtures thereof.

In one embodiment of the method disclosed herein above anionic surfactant (b) is a dialkyl sulfosuccinate the following formula:

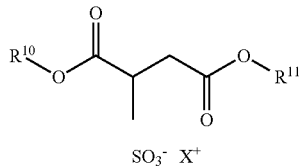

IV where $R^{10}$ and $R^{11}$ are the same or different linear or branched $C_6$ to $C_{10}$ alkyl groups and X is a sodium ion, a potassium ion, a lithium ion, or an ammonium ion, preferably the dialkyl sulfosuccinate is 1,4-bis(2-ethylhexyl) sodium sulfosuccinate.

In one embodiment of the method disclosed herein above the anionic surfactant (b) is a di-sulfonate the following formula:

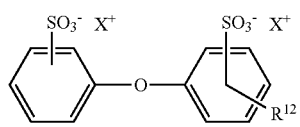

V where $R^{12}$ is a $C_3$ to $C_{20}$ alkyl radical, preferably propyl, butyl, octyl, nonyl, decyl, or dodecyl, preferably a $C_8$ to $C_{12}$ alkyl radical and X is a sodium ion, a potassium ion, a lithium ion, or an ammonium ion, preferably the di-sulfonate is selected from butyl diphenyl ether disulfonic acid sodium, nonyl diphenyl ether disulfonic acid sodium, dodecyl diphenyl ether disulfonic acid sodium, dodecyl diphenyl ether disulfonic acid potassium, butyl diphenyl ether disulfonic acid lithium, nonyl diphenyl ether disulfonic acid ammonium, dodecyl diphenyl ether disulfonic acid ammonium, dodecyl diphenyl ether disulfonic acid lithium, or mixtures thereof.

In one embodiment of the method disclosed herein above the aqueous sulfide-scavenging composition further comprises an alcohol, a glycol ether, or mixtures thereof.

DETAILED DESCRIPTION OF THE INVENTION

The method of the present invention uses an aqueous sulfide-scavenging composition comprising: (a) one or more triazine compound, (b) one or more anionic surfactant, and (c) optionally an alcohol, a glycol ether, or mixtures thereof. The compositions provide excellent sulfide scavenging in the context of sulfide removal from oil liquid or gas streams, and in the treatment of oil or gas transmission lines or equipment. The compositions are capable of scavenging a wide variety of sulfur-bearing compounds, such as sulfhydryl compounds including hydrogen sulfide and organic sulfides (e.g., mercaptans, thiols, and sulfur-bearing carboxylic acids). The description, method of preparation, and use are described in detail below.

Triazine compounds and methods to make them are well known, for example see U.S. Pat. No. 5,744,024, which is incorporated by reference herein in its entirety. Suitable triazine compounds include alkyl hexahydro triazines, alkoxy-hexahydro triazins, and hydroxyalkyl-hexahydro triazines.

Suitable alkyl hexahydro-triazines have the following formula:

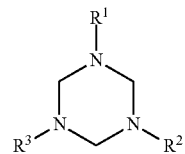

I where $R^1$, $R^2$, and $R^3$ are the same or different and are independently selected from a $C_1$ to $C_{20}$ straight or branched chain alkyl group, preferably a $C_1$ to $C_6$ straight or branched chain alkyl group, and more preferably a a $C_1$ to $C_4$ straight or branched chain alkyl group. The preferred alkyl hexahydro-triazine is 1,3,5-trimethyl-hexahydro-1,3,5-triazine where $R^1$, $R^2$, and $R^3$ are all a $C_1$ alkyl group.

Suitable alkyl hexahydro-triazines have the following formula:

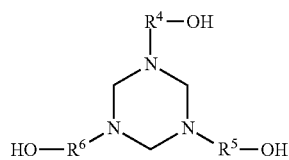

II where $R^4$, $R^5$, and $R^6$ may be the same or different and are independently selected from a $C_1$ to $C_6$ alkyl group, preferably $C_1$ to $C_4$. The preferred triazine of this group is 1,3,5-tri-(2-hexahydroethyl)-hexahydro-s-triazine where $R^4$, $R^5$, and $R^6$ are all a $C_2$ alkyl group.

Suitable alkoxy-hexahydro triazines have the following formula:

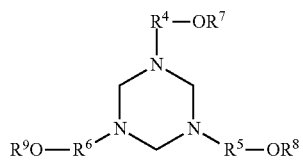

III where $R^4$, $R^5$, and $R^6$ are described herein above and $R^7$, $R^8$, and $R^9$ are independently selected from a $C_1$ to $C_6$ alkyl group, preferably $C_1$.

The preferred hexahydro-triazine is 1,3,5-tri-methoxypropyl-hexahydro-1,3,5-triazine (MOPA hexahydro-triazine).

The MOPA-hexahydro-triazine is prepared by the condensation of methoxypropyl amine (MOPA) with formalin or a lower aldehyde such as formaldehyde. As noted above, the hexahydro-triazine scavenger can be used as manufactured (water solution). For use in oil base formulations, the scavenger can be used in neat form or dissolved in a suitable solvent.

Although the preferred hexahydro-triazine is the MOPA hexahydro-triazine, other hexahydro-triazines within the scope of Formula III include 1,3,5-tri-methoxyethyl-hexahydro-1,3,5-triazine (from 2-methoxyethyl amine); 1,3,5- tri-(3-ethoxypropyl)-hexahydro-1,3,5-triazine (from 3-ethoxypropylamine); 1,3,5-tri-(3-isopropoxypropyl)-hexahydro-1,3,5-triazine (from 3-ethoxypropylamine); 1,3,5-(3-butoxy-propyl)-hexahydro-1,3,5-triazine (from 3 butoxypropylamine); 1,3,5-tri-(3-butoxypropyl)-hexahydro-1,3,5-triazine (from 3-butoxypropylamine); and 1,3,5-tri-(5-methoxypentyl)-hexahydro-1,3,5-triazine (from 5-methoxypentylamine).

The triazine compound is used in the aqueous sulfide-scavenging composition in an amount equal to or greater than 5 weight percent, preferably equal to or greater than 15 weight percent, more preferably equal to or greater than 25 weight percent, and more preferably equal to or greater than 35 weight percent based on the total weight of the aqueous sulfide-scavenging composition. The triazine compound is used in the aqueous sulfide-scavenging composition in an amount equal to or less than 90 weight percent, preferably equal to or less than 80 weight percent, more preferably equal to or less than 60 weight percent, and more preferably equal to or less than 40 weight percent based on the total weight of the aqueous sulfide-scavenging composition.

Anionic surfactants are well known, for example see U.S. Pat. No. 4,426,303, in which an anionic surfactant alkylated diaromatic sulfonate is used in enhanced oil recovery processes. U.S. Pat. No. 8,828,124 disclosed the use of an anionic surfactant for biogas purification. WO 2014116309 discloses the use of anionic surfactants and polyalkylenimine for sweep efficiency improvement of a fluid flood of a reservoir.

Suitable anionic surfactants include carboxylates, sulfonates, di-sulfonates, petroleum sulphonates, alkylbenzenesulphonates, naphthalenesulphonates, olefin sulphonates, alkyl sulphates, sulphates, sulphated natural oils and fats, sulphated esters, sulphated alkanolamides, alkylphenols, ethoxylated alkylphenols, and sulphated alkylphenols.

Suitable dialkyl sulfosuccinates have the following formula:

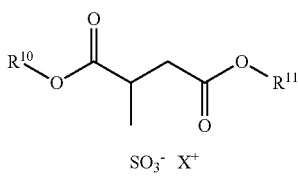

IV where $R^{10}$ and $R^{11}$ are the same or different linear or branched $C_6$ to $C_{10}$ alkyl groups and X is a monovalent or divalent cation, preferably sodium ion, potassium ion, lithium ion, or ammonium ion including ammonium, methyl ammonium, ethyl ammonium, dimethyl ammonium, methylethyl ammonium, trimethyl ammonium, dimethylbutyl ammonium, hydroxylethyl ammonium, and methylhydroxyethyl ammonium.

A preferred sulfouccinate is 1,4-bis(2-ethylhexyl) sodium sulfosuccinate. 1,4-bis(2-ethylhexyl) sodium sulfosuccinate is available blended with water/isopropanol as TRITON® GR-5M Surfactant from The Dow Chemical Company, or blended with petroleum distillate available as TRITON GR-7M Surfactant from The Dow Chemical Company, or blened with aromatic hydrocarbon available as TRITON GR-7ME Surfactant from The Dow Chemical Company.

Suitable di-sulfonates have the following formula:

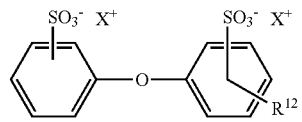

V where $R^{12}$ is a $C_3$ to $C_{20}$ alkyl radical, preferably propyl, butyl, octyl, nonyl, decyl, or dodecyl, preferably a $C_8$ to $C_{12}$ alkyl radical and X is as described herein above.

Preferred di-sulfonates include butyl diphenyl ether disulfonic acid sodium, nonyl diphenyl ether disulfonic acid sodium, dodecyl diphenyl ether disulfonic acid sodium, dodecyl diphenyl ether disulfonic acid potassium, butyl diphenyl ether disulfonic acid lithium, nonyl diphenyl ether disulfonic acid ammonium, dodecyl diphenyl ether disulfonic acid ammonium, dodecyl diphenyl ether disulfonic acid lithium, and mixtures thereof.

Suitable alkylbenzene sulfonates have the following formula:

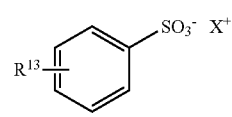

VI where $R^{13}$ may be a linear or a branched $C_1$ to $C_{20}$ alkyl group, preferably $C_4$ to $C_{15}$, most preferably $C_{11}$ and X is as described herein above. A preferred alkylbenzene sulfonate is sodium dodecylbenzenesulfonate.

Suitable alkyl sulfates have the following formula:

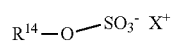

VII where $R^{14}$ may be a linear or a branched $C_1$ to $C_{20}$ alkyl group, preferably $C_8$ to $C_{20}$, most preferably $C_{12}$ and X is as described herein above. Preferred alkyl sulfonates are the sodium salt of dodecyl sulfate and the ammonium salt of dodecyl sulfate.

Suitable sulfates have the following formula:

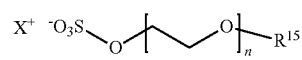

VIII where $R^{15}$ may be a linear or a branched $C_1$ to $C_{20}$ alkyl group, preferably $C_4$ to $C_{20}$, most preferably $C_{12}$ and X is as described herein above. A preferred sulfate is sodium lauryl ether ether sulfate.

Suitable carboxylates have the following formula:

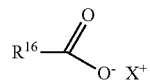

IX where $R^{16}$ may be a linear or a branched $C_1$ to $C_{20}$ alkyl group, preferably $C_8$ to $C_{20}$, most preferably $C_{17}$ and X is as described herein above. A preferred carboxylate is sodium octadecanoate.

The anionic surfactant is used in the aqueous sulfide-scavenging composition in an amount equal to or greater than 0.1 weight percent, preferably equal to or greater than 1 weight percent, preferably equal to or greater than 2 weight percent, and more preferably equal to or greater than 3 weight percent based on the total weight of the aqueous sulfide-scavenging composition. The anionic surfactant is used in the aqueous sulfide-scavenging composition in an amount equal to or less than 50 weight percent, preferably equal to or less than 30 weight percent, preferably equal to or less than 20 weight percent, preferably equal to or less than 10 weight percent, and more preferably equal to or less than 5 weight percent based on the total weight of the aqueous sulfide-scavenging composition.

In one embodiment of the present invention, the scavenging composition comprises a glycol ether. The glycol ethers usable in the compositions of the invention are preferably selected from the group consisting of glycol mono-, di-, and tri-alkylene ethers, glycol aryl ethers, derivatives of the foregoing, and mixtures thereof, where the alkylene groups may be straight or branched chain, and the aryl groups may be any aromatic species, such as mono- or poly-phenyls. The derivatives may again be any form of the foregoing ethers, such as the acetates, acylates, amides, and nitriles. The single most preferred glycol ether for use in the invention is glycol butyl ether, also known as 2-butoxyethanol. However, other glycol ethers may also be used, alone or in combination, for example: ethylene glycol monomethyl ether (EGME) or 2-methoxyethanol, ethylene glycol monoethyl ether (EGEE) or 2-ethoxyethanol, ethylene glycol monoethyl ether acetate (EGEEA) or 2-ethoxyethanol acetate, ethylene glycol monobutyl ether acetate (EGBEA) or 2-butoxyethanol acetate, ethylene glycol monopropyl ether (EGPE) or 2-propoxyethanol, ethylene glycol monophenyl ether (EGPhE) or 2-phenoxyethanol, ethylene glycol monohexyl ether or 2-hexyloxyethanol, ethylene glycol mono 2-ethylhexyl ether or 2-(2-ethylhexyloxy) ethanol.

The glycol component is normally present in the compositions of the invention at a level of from 0 to 90 percent by volume, and more preferably from 0 to 50 percent by volume.

In one embodiment of the present invention, the scavenging composition comprise an alcohol component. The alcohol component, when used, is preferably an organic mono- or poly-alcohol including a $C_1$ to $C_{18}$ organic moiety. More preferably, the alcohol is a $C_1$ to $C_6$ mono-alcohol, where the $C_1$ to $C_6$ group is a straight or branched chain alkyl group. The most preferred alcohols are selected from methanol, ethanol, propanol, isopropanol, butanol, and mixtures thereof, with methanol normally being used.

The alcohol component is normally present in the compositions of the invention at a level of from 0 to 90 percent by volume, and more preferably from 0.1 to 20 percent by volume.

The balance of the aqueous sulfide-scavenging composition is water, typically from 0.1 to 90 percent by volume, preferably from 1 to 80 percent by volume.

The scavenging compositions of the invention can be used in a variety of ways in order to reduce or substantially eliminate $H_2S$ and other objectionable sulfides from hydrocarbon streams (e.g., crude oil or natural gas), and to scavenge hydrocarbon transmission lines or equipment (e.g., well heads, separators, glycol units, coolers, and compressors).

For example, the present scavenging compositions may be employed with "in-line" injection systems to reduce the hydrogen sulfide level in sour gas streams. The scavenging compositions may be injected at any point in-line which will provide the compositions the opportunity to react with a gaseous or liquid hydrocarbon stream, e.g., at the well-head, at the or separators. In such an in-line injection system, the temperature and pressure of the gas system is not critical for the success of the scavenging method. Accordingly, within wide limits, the existing system conditions need not be altered for effective scavenging.

When using an in-line injection method for sweetening natural gas, the scavenging compositions of the invention may be injected directly into the flow line at a rate of between about 0.3 to about 1.0 gallons per ppm hydrogen sulfide per MMSCF of gas. However, the rate of injection may be varied from system to system, as will be evident to one skilled in the art.

The compositions of the invention may also be used with $H_2S$ scrubber or bubble towers, or in chemical solvent processes. In each of these systems, towers are used to increase the contact time between the scavenging compositions and the gaseous hydrocarbon stream, thereby improving efficiencies over in-line systems.

In scrubber/bubble tower systems, the scavenging compositions are preferably used without further dilution, or with additional alcohol or other non-aqueous solvents. The hydrocarbon stream is then delivered to the bottom of the tower and passes upwardly through the diluted scavenging composition to effect the desired result. Such tower systems are the preferred apparatus in which to sweeten hydrocarbon streams, owing to the high efficiencies and relatively low capital investments of such systems. Use of the present composition permits gas sweetening without carryover of water vapor, which minimizes and eliminates corrosion in downstream equipment.

In chemical solvent processes, the sulfides are stripped from the scavenging compositions after the sweetening reaction. Accordingly, in such systems, the compositions may be part of continuous, recirculating processes, and may be regenerated and reused. The amounts of the scavenging compositions are variable depending upon the particular application (e.g., the tower sizes and the amounts of sulfides present, etc.).

Operators also periodically treat their empty flow lines and equipment with sulfide scavengers in order to scavenge residual sulfides on the surfaces of the lines and equipment. This is done by spraying the scavenger onto these surfaces using a moving spray head. The compositions of the invention are very well suited for such spray treatments, and, owing to the low moister contents of the compositions, minimize corrosion problems which have plagued prior aqueous triazine scavengers.

EXAMPLES

In the following procedure is followed to determine the amount of $H_2S$ scavenging. To a 22 mL vial is added 19 mL of SOLVESSO™ 150 (aromatic solvent primarily $C_{10}$ to $C_{12}$ alkyl benzenes) and 0.5 mL of $H_2S$ is injected and the mixture is shaken for 1 hour to ensure gas-liquid-equilibrium. Scavenger solutions are injected into the vial and the vial is vigorously shaken for 5 min and the $H_2S$ concentration of the headspace of the vial is analyzed by gas chromatography (GC). 0.5 mL of gas in the headspace of the vial is withdrawn and injected through the sample injection port of the effluent gas line of the GC. The GC is a SIEVERS™ Model 355 GC available from Ionics Instruments using a 60-m by 0.53 mm Restek MXT-1, 0.53 mm ID, 7 micron capillary column from Restek equipped with a Sulfur Chemiluminescence Detector. $N_2$ is used as the effluent gas. The peak with a residence time of 1.2 minute corresponds to $H_2S$, the concentration of which is calibrated using 100 ppm and 10 ppm $H_2S$ in $N_2$. The headspace of the vial is analyzed by GC again after 1 h.

The composition for Examples 1 and Comparative Examples A to F are listed in Table 1. In Table 1:

"MEA" is a 34 weight percent aqueous solution of 1,3,5-tris(2-hydroxyethyl)-hexahydro-s-triazine in water and "GR-5M" is 60 weight percent dioctyl sodium sulfosuccinate blended with water/isopropanol and is available as TRITON GR-5M Surfactant from The Dow Chemical Company.

TABLE 1

|  | MEA, mg | GR-5M, mg | [H$_2$S] @ 5 min, ppm | [H$_2$S] @ 1 h, ppm |
|---|---|---|---|---|
| Com. Ex. A |  |  | 1450 | 1300 |
| Com. Ex. B | 32.7 |  | 720 | 385 |
| Com. Ex. C | 144 |  | 21 | 0 |
| Com. Ex. D | 217 |  | 15 | 0 |
| Com. Ex. E | 288 |  | 2.7 | 0 |
| Com. Ex. F |  | 28.8 | 1430 | 905 |
| Ex. 1 | 27.2 | 1.43 | 39 | 0 |

It is apparent that the example of the aqueous sulfide-scavenging composition of the present invention scavenges $H_2S$ much faster than either of its components at a similar dosage. It requires a significantly higher dosage of the MEA alone to achieve a similar result in the first 5 min.

What is claimed is:

1. A method of reducing $H_2S$ in a liquid or gaseous stream comprising $H_2S$ which comprises contacting the stream with an aqueous sulfide-scavenging composition comprising:
    (a) one or more triazine compound of the formula:

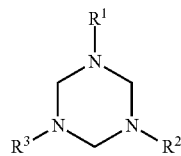

wherein $R^1$, $R^2$, and $R^3$ are independently selected from a $C_1$ to $C_{20}$ straight or branched chain alkyl group,

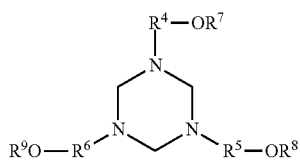

wherein $R^4$, $R^5$, and $R^6$ are independently selected from a $C_1$ to $C_6$ alkyl group and wherein $R^7$, $R^8$, and $R^9$ are independently selected from hydrogen or a $C_1$ to $C_6$ alkyl group,
and
    (b) an anionic surfactant selected from a dialkyl sulfosuccinate, a di-sulfonate, an alkylbenzene sulfonate, an alkyl sulfate, a carboxylic acid, or mixtures thereof, wherein the amount of the anionic surfactant is sufficient to accelerate the $H_2S$ scavenging action of the triazine compound in comparison with the scavenging action of said triazine without the surfactant compound.

2. The method of claim 1 wherein the triazine compound (a) is 1, 3, 5-trimethyl-hexahydro-1, 3, 5-triazine or 1, 3, 5-tris(2-hydroxyethyl)hexahydro-s-triazine.

3. The method of claim 1 wherein the anionic surfactant (b) is a dialkyl sulfosuccinate of the following formula:

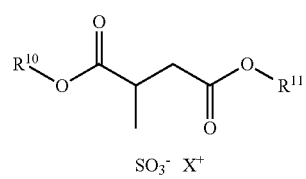

where $R^{10}$ and $R^{11}$ are the same or different linear or branched $C_6$ to $C_{10}$ alkyl groups and X is a sodium ion, a potassium ion, a lithium ion, or an ammonium ion.

4. The method of claim 3 wherein the dialkyl sulfosuccinate is 1,4-bis(2-ethylhexyl) sodium sulfosuccinate.

5. The method of claim 1 wherein the anionic surfactant (b) is a di-sulfonate of the following formula:

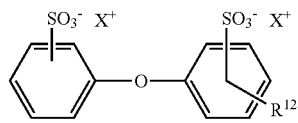

where $R^{12}$ is a $C_3$ to $C_{20}$ alkyl radical, preferably propyl, butyl, octyl, nonyl, decyl, or dodecyl, preferably a $C_8$ to $C_{12}$ alkyl radical and X is a sodium ion, a potassium ion, a lithium ion, or an ammonium ion.

6. The method of claim 5 wherein the di-sulfonate is selected from butyl diphenyl ether disulfonic acid sodium, nonyl diphenyl ether disulfonic acid sodium, dodecyl diphenyl ether disulfonic acid sodium, dodecyl diphenyl ether disulfonic acid potassium, butyl diphenyl ether disulfonic acid lithium, nonyl diphenyl ether disulfonic acid ammonium, dodecyl diphenyl ether disulfonic acid ammonium, dodecyl diphenyl ether disulfonic acid lithium, or mixtures thereof.

7. The method of claim 1 wherein the aqueous sulfide-scavenging composition further comprises an alcohol, a glycol ether, or mixtures thereof.

* * * * *